(12) United States Patent
Mueller

(10) Patent No.: US 9,770,255 B2
(45) Date of Patent: Sep. 26, 2017

(54) ONE-PIECE HANDLE ASSEMBLY

(71) Applicant: Covidien LP, Mansfield, MA (US)

(72) Inventor: Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1123 days.

(21) Appl. No.: 13/868,732

(22) Filed: Apr. 23, 2013

(65) Prior Publication Data
US 2013/0345735 A1 Dec. 26, 2013

Related U.S. Application Data

(60) Provisional application No. 61/644,528, filed on Jun. 26, 2012.

(51) Int. Cl.
*A61B 17/29* (2006.01)
*B23P 11/00* (2006.01)
(Continued)

(52) U.S. Cl.
CPC ........ *A61B 17/2909* (2013.01); *A61B 17/282* (2013.01); *A61B 17/2816* (2013.01); *A61B 17/2841* (2013.01); *A61B 17/295* (2013.01); *A61B 18/1445* (2013.01); *B23P 11/00* (2013.01); *A61B 2017/00526* (2013.01);
(Continued)

(58) Field of Classification Search
CPC ... A61B 17/29; A61B 17/2909; A61B 17/295; A61B 2017/2919; A61B 2017/2948; A61B 17/28; A61B 17/2812; A61B 17/2816; A61B 17/2841; A61B 17/285; A61B 2017/2845
See application file for complete search history.

(56) References Cited

U.S. PATENT DOCUMENTS

D249,549 S   9/1978 Pike
D263,020 S   2/1982 Rau, III
(Continued)

FOREIGN PATENT DOCUMENTS

CN   201299462   9/2009
DE   2415263     10/1975
(Continued)

OTHER PUBLICATIONS

Extended European Search Report corresponding to EP 13 17 3352.9, completed Sep. 27, 2013 and mailed Oct. 7, 2013; (7 pp).
(Continued)

*Primary Examiner* — Katherine Rodjom

(57) ABSTRACT

A one-piece handle assembly and a method of assembling the one-piece handle assembly. The one-piece handle assembly includes an outer tube connected to a fixed jaw and an inner tube connected to a moveable jaw. The inner tube is installed within the outer tube. The surgical instrument assembly further includes a handle body overmolded onto the outer tube and a handle grip connected to the handle body. The handle grip controls movement of the moveable jaw along an axis about defined through the outer tube. The one-piece handle assembly further includes a knife plunger for controlling activation of a knife rod assembly. The one-piece handle assembly is void of any welds, adhesives, or fasteners to complete the final assembly of the one-piece handle assembly.

16 Claims, 7 Drawing Sheets

(51) Int. Cl.
*A61B 17/28* (2006.01)
*A61B 17/295* (2006.01)
*A61B 18/14* (2006.01)
*A61B 17/00* (2006.01)
*A61B 18/00* (2006.01)

(52) U.S. Cl.
CPC . *A61B 2017/292* (2013.01); *A61B 2017/2916* (2013.01); *A61B 2018/0091* (2013.01); *A61B 2018/1455* (2013.01); *Y10T 29/49002* (2015.01); *Y10T 29/49826* (2015.01); *Y10T 29/49863* (2015.01); *Y10T 29/49959* (2015.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| 5,342,390 A | 8/1994 | Slater et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 2006/0241532 A1 | 10/2006 | Murakami |
| 2007/0135733 A1* | 6/2007 | Soukup ............ A61M 25/0136 600/585 |
| 2010/0145334 A1* | 6/2010 | Olson ................ A61B 18/1445 606/48 |
| 2012/0209254 A1* | 8/2012 | Park .................. A61B 17/2909 606/1 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0897696 A1 | 2/1999 |
| EP | 1159926 | 12/2001 |
| EP | 1 607 046 | 12/2005 |
| EP | 1 810 625 | 7/2007 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |

(56) References Cited

FOREIGN PATENT DOCUMENTS

| JP | 2004-528869 | 9/2004 |
|---|---|---|
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |
| WO | WO 2008/097789 | 8/2008 |

OTHER PUBLICATIONS

U.S. Appl. No. 08/926,869, filed Sep. 10, 1997.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, 6/920/00, Thomas P. Ryan.
U.S. Appl. No. 12/336,970, filed Dec. 17, 2008, Paul R. Sremeich.
U.S. Appl. No. 13/277,373, filed Oct. 20, 2011, Glenn A. Horner.
U.S. Appl. No. 13/277,926, filed Oct. 20, 2011, David M. Garrison
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/663,317, filed Oct. 29, 2012, Unger.
U.S. Appl. No. 13/708,335, filed Dec. 7, 2012, Dumbauld.
U.S. Appl. No. 13/711,201, filed Dec. 11, 2012, Regadas.
U.S. Appl. No. 13/736,650, filed Jan. 8, 2013, McKenna.
U.S. Appl. No. 13/741,550, filed Jan. 15, 2013, Deborski.
U.S. Appl. No. 13/747,090, filed Jan. 22, 2013, Romero.
U.S. Appl. No. 13/747,167, filed Jan. 22, 2013, Romero.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
EP Examination Report dated Apr. 29, 2015 from European Appl. No. 13173352.9.

\* cited by examiner

ONE-PIECE HANDLE ASSEMBLY

CROSS REFERENCE TO RELATED APPLICATION

The present application claims the benefit of and priority to U.S. Provisional Application Ser. No. 61/664,528, filed on Jun. 26, 2012, the entire contents of which are incorporated herein by reference.

BACKGROUND

The present disclosure relates to surgical instruments and, more particularly, to a one-piece handle assembly for use with a surgical instrument.

TECHNICAL FIELD

Electrosurgical instruments, e.g., endoscopic forceps, are well known in the medical arts and typically include a housing, a handle assembly including a movable handle, a shaft and an end effector assembly attached to a distal end of the shaft. The end effector includes jaw members configured to manipulate tissue (e.g., grasp and seal tissue). Typically, the endoscopic forceps utilizes both mechanical clamping action and electrical energy to effect hemostasis by heating the tissue and blood vessels to coagulate, cauterize, seal, cut, desiccate, and/or fulgurate tissue. Usually, one or more driving mechanisms, e.g., a drive assembly including a drive element, is utilized to cooperate with one or more components operatively associated with the handle assembly to impart movement to one or both of the jaw members. To facilitate positioning the jaw members about tissue, the endoscopic forceps sometimes includes a rotating assembly. The rotating assembly is usually operably coupled to the shaft and configured such that rotation of the rotating assembly rotates the shaft including the jaw members thereon in a predetermined direction, e.g., approximately 180° in either a clockwise or counterclockwise direction.

Within the shaft are multiple coaxial tubes in communication with the end effector components and the corresponding actuators/linkages in the handle assembly. For example a blade wire may be present inside the shaft, and is in communication with the handle assembly and a knife blade container within the end effector for cutting tissue.

The handle assembly is generally of a rigid structure containing a handle, trigger, and switches therein for moving the end effector assembly, knife deployment, and electrosurgical activation of the end effector assembly.

SUMMARY

In accordance with one aspect of the present disclosure, a one-piece handle assembly and a method of assembling the one-piece handle assembly. The one-piece handle assembly includes an outer tube connected to a fixed jaw and an inner tube connected to a moveable jaw. The inner tube is installed within the outer tube. The surgical instrument assembly further includes a handle body over molded onto the outer tube and a handle grip connected to the handle body. The handle grip controls movement of the moveable jaw by moving perpendicular to a shaft axis about a fulcrum. The one-piece handle assembly further includes a knife plunger for controlling activation of a knife rod assembly. The one-piece handle assembly is void of any welds, adhesives, or fasteners to complete the final assembly of the one-piece handle assembly.

In accordance with another aspect of the present disclosure, a method for assembling a surgical instrument includes the steps of attaching a fixed jaw to an outer tube and overmolding a handle body to the outer tube. The method further includes the step of inserting a grip pivot pin to connect a handle grip to the handle body. The grip pivot pin includes a cam surface. The method further includes the step of and connecting a moving jaw to the fixed jaw while engaging an inner tube to control the moving jaw.

The method may further include that the fixed jaw is connected to the moving jaw using an end effector pivot pin at pivot point between the fixed jaw and the moving jaw.

Alternatively or in addition, the method may include the steps of overmolding a bushing to the inner tube and sliding a jaw spring over the inner tube, wherein a proximal end of the jaw spring contacts the bushing. The method may also include the steps of sliding the inner tube through a spring cartridge bore in a spring cartridge and sliding the inner tube into the outer tube.

Alternatively or in addition, the method may include the steps of sliding a knife plunger through a handle body bore in the handle body and aligning a cross bore on the knife plunger with an assembly bore in the handle body. The method may also include the steps of aligning a relief slot on the handle grip with the assembly bore and inserting an assembly pin into the assembly bore to engage the knife plunger and the handle grip. Further, the method may include the steps of attaching a knife retainer to a knife rod and sliding a knife spring over the knife rod and against a knife retainer to create a knife rod assembly. The method may also include inserting a knife guide into the inner tube and inserting the knife rod assembly into a proximal end of the knife guide.

Alternatively or in addition, the method may include the step of attaching a plunger cap to the knife plunger.

Alternatively or in addition, the method may include the steps of compressing the bushing distally prior to inserting the assembly pin and releasing the compression after inserting the assembly pin.

Alternatively or in addition, the method may include the step of aligning two flanges on the plunger cap with two flat surfaces on the handle body, when inserting the assembly pin.

Alternatively or in addition, the method may include that the two flanges limit rotation of the knife plunger about an axis defined therethrough.

Alternatively or in addition, the method may include the step of aligning the spring cartridge with assembly bore, when inserting the assembly pin.

Alternatively or in addition, the method may include the step of preventing the knife plunger from travelling distally except for when the fixed jaw and the moveable jaw are in a closed position.

Alternatively or in addition, the method may include the steps of routing electrical wires from the fixed jaw and the moveable jaw through the surgical instrument and providing a cable to connect the surgical instrument to a generator.

In accordance with another aspect of the present disclosure, a surgical instrument assembly includes an outer tube connected to a fixed jaw. The outer tube having a longitudinal axis defined therethrough. The surgical instrument assembly further includes an inner tube connected to a moveable jaw. The inner tube is coaxially-disposed the outer tube. The surgical instrument assembly further includes a handle body over molded onto the outer tube and a handle grip connected to the handle body. The handle grip controls movement of the moveable jaw by moving perpendicular to a shaft axis about a fulcrum.

According to another aspect of the present disclosure, the surgical instrument assembly is devoid of any welds, adhesives, or fasteners to complete the final assembly of the surgical instrument assembly.

According to a further aspect of the present disclosure, the fulcrum is a bore defined in the handle body configured to receive a grip pivot pin.

According to another aspect of the present disclosure, the surgical instrument includes a knife guide inserted within the inner tube, a knife plunger installed within the handle body; and a knife rod assembly inserted within the knife guide and the knife plunger, wherein the knife plunger controls activation of the knife rod assembly.

According to a further aspect of the present disclosure, the knife rod assembly includes a knife rod and a knife rod retainer According to another aspect of the present disclosure, the knife plunger includes two flanges separated by a distance approximately equal to an outer width of the handle grip, the two flanges configured to prevent the knife plunger from rotating about the longitudinal axis defined within the handle body and the outer tube.

In another aspect, a method of assembling a surgical instrument assembly includes the step of connecting an outer tube to a fixed jaw. The outer tube includes an axis defined therethrough. The method further includes the step of connecting an inner tube to a moveable jaw. The inner tube is coaxially-disposed within the outer tube. The method further includes the steps of overmolding a handle body onto the outer tube and connecting a handle grip to the handle body. The handle grip controls movement of the moveable jaw by moving perpendicular to a shaft axis about a fulcrum.

The method may further include the steps of inserting a knife guide within the inner tube and installing a knife plunger within the handle body. The method may further include the step of inserting a knife rod assembly inserted within the knife guide and the knife plunger. The knife plunger controls activation of the knife rod assembly. The method may also include the step of attaching a plunger cap to the knife plunger.

Alternatively or in addition, the method may include the step of routing electrical wires through the inner tube and the outer tube to the movable jaw and the fixed jaw. The electrical wires configured to connect to a generator.

As used herein, the term "distal" refers to the portion that is being described which is further from a user, while the term "proximal" refers to the portion that is being described which is closer to a user.

BRIEF DESCRIPTION OF THE DRAWINGS

Various embodiments of the present disclosure are described herein with reference to the drawings wherein.

DETAILED DESCRIPTION

Figure 1:
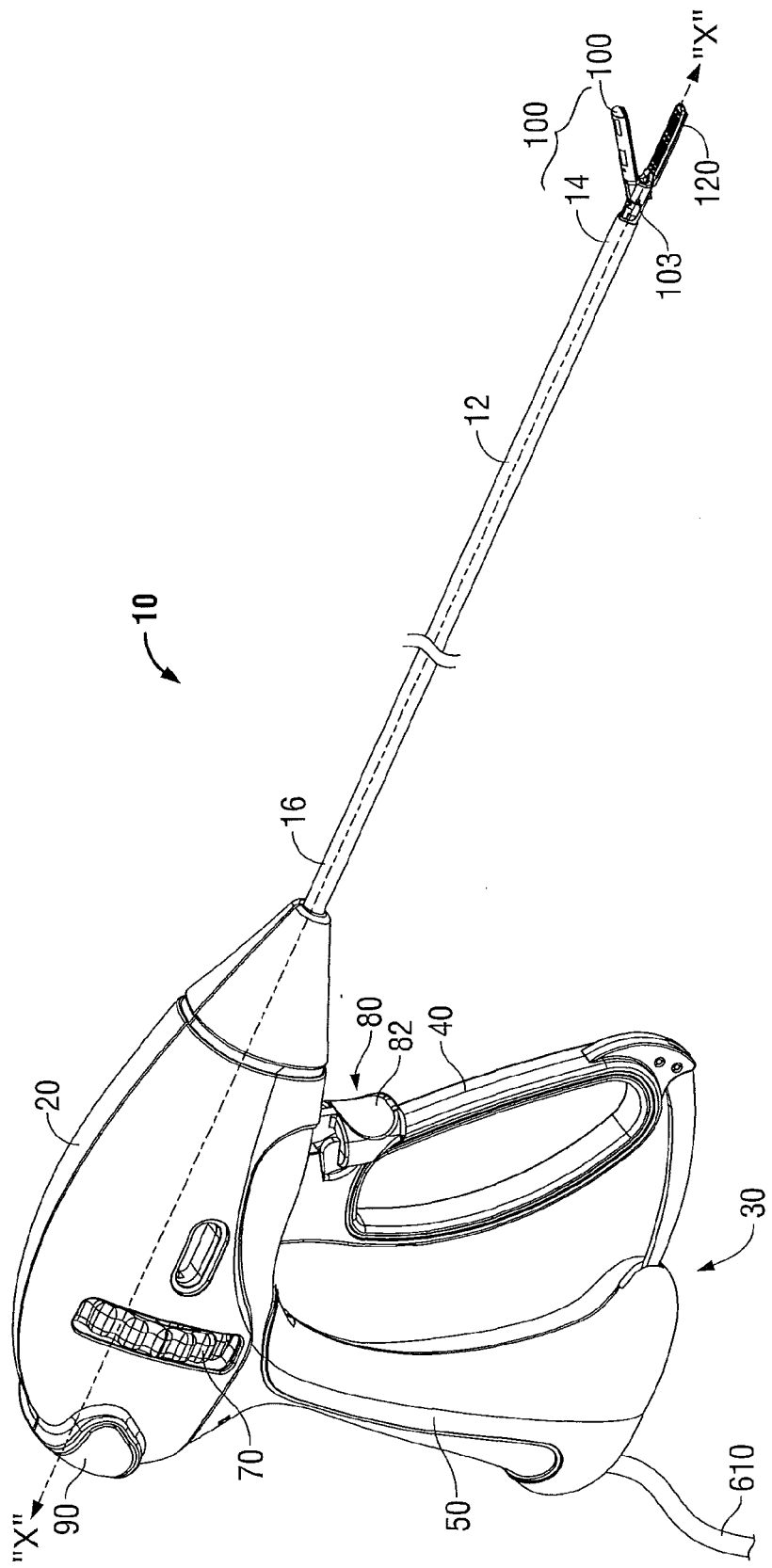
FIG. 1 is a front, perspective view of an endoscopic surgical instrument configured for use in accordance with the present disclosure.
Figure 2:
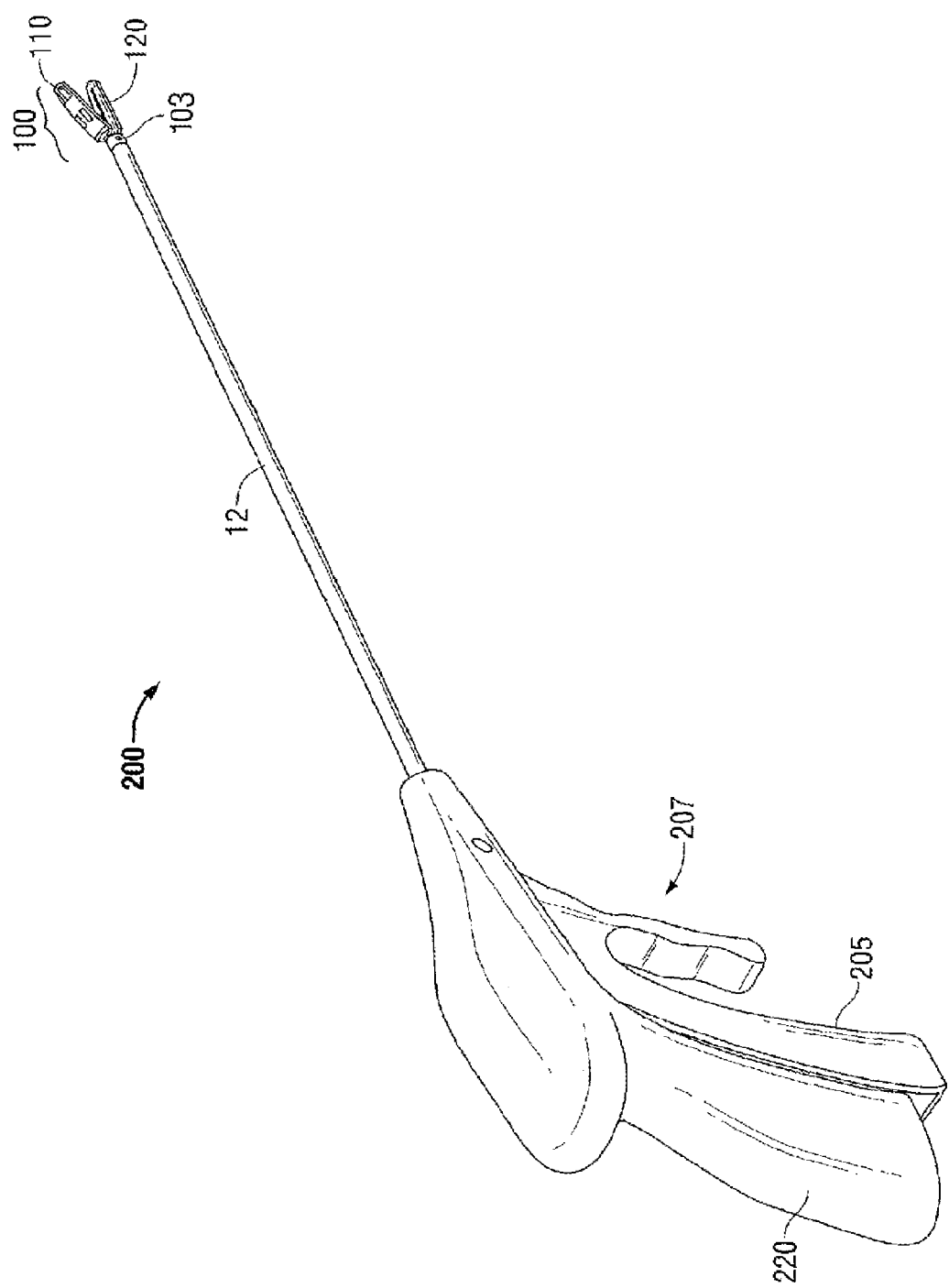
FIG. 2 is an external, perspective view of an endoscopic surgical instrument with a one-piece handle assembly configured for use in accordance with the present disclosure.
Figure 3:
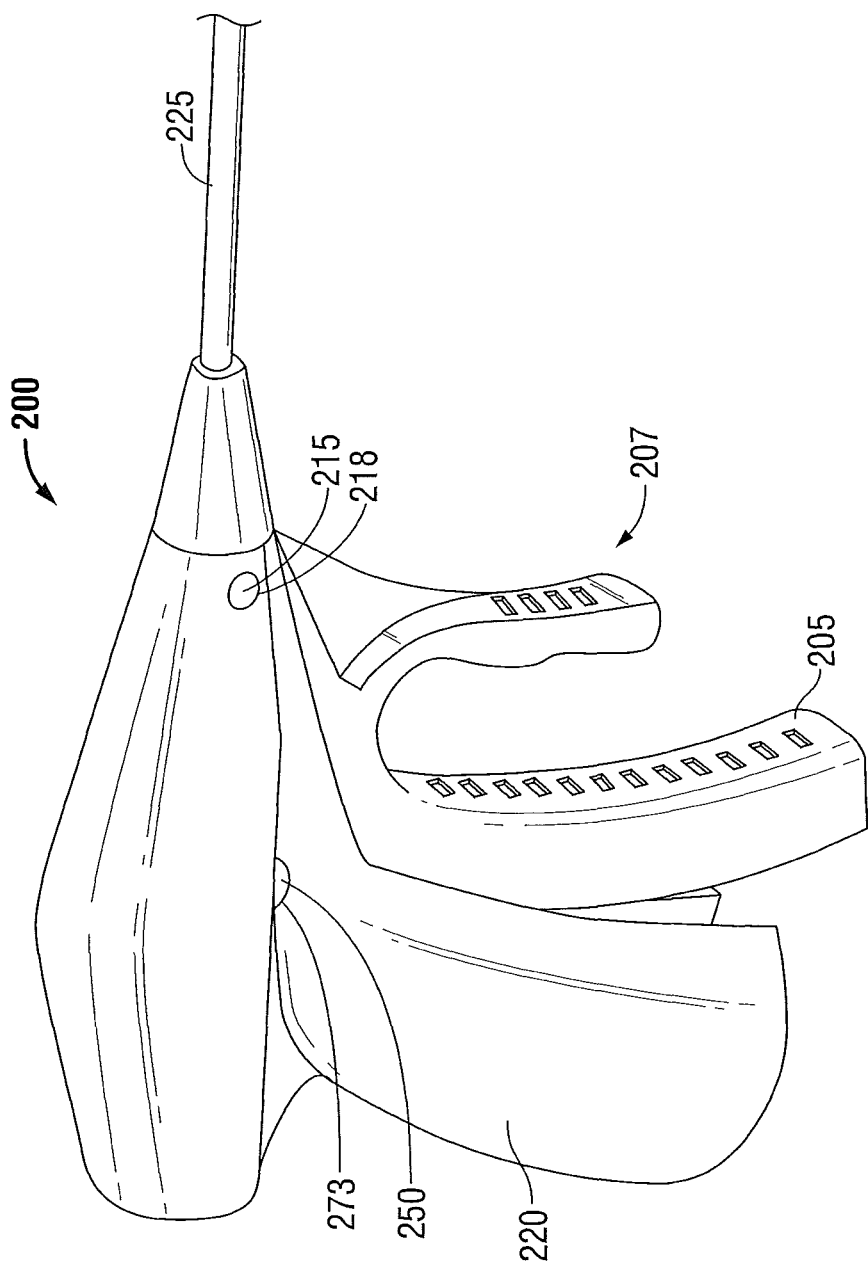
FIG. 3 is an external, perspective view of a one-piece handle assembly configured for use in accordance with the present disclosure.

Embodiments of the present disclosure are described in detail with reference to the drawing figures wherein like reference numerals identify similar or identical elements.

FIG. 1 depicts a forceps 10 for use in connection with endoscopic surgical procedures. The endoscopic forceps 10 is provided defining a longitudinal axis "X-X" and including a housing 20, a handle assembly 30, a rotating assembly 70, a trigger assembly 80, an activation switch 90, and an end effector assembly 100. Forceps 10 further includes a shaft 12 having a distal end 14 configured to mechanically engage end effector assembly 100 and a proximal end 16 that mechanically engages housing 20. Housing 20 contains the internal working components of the forceps 10 which are not described herein but which may be found in commonly-owned U.S. Pat. No. 7,156,846, the entire contents of which are hereby incorporated by reference herein.

End effector assembly 100 is shown attached at a distal end 14 of shaft 12 and includes a pair of opposing jaw members 110 and 120. Jaw members 110, 120 are moveable between a spaced-apart position and an approximated position for grasping tissue therebetween. End effector assembly 100 is designed as a unilateral assembly, i.e., where jaw member 120 is fixed relative to shaft 12 and jaw member 110 is moveable about a pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12.

With continued reference to FIG. 1, forceps 10 also includes electrosurgical cable 610 that connects forceps 10 to a generator (not shown) or other suitable power source, although forceps 10 may alternatively be configured as a battery powered instrument. Cable 610 includes a wire (or wires) (not explicitly shown) extending therethrough that has sufficient length to extend through shaft 12 in order to provide energy to at least one of the jaw members 110 and 120 of end effector assembly 100. Trigger 82 of trigger assembly 80 may be selectively depressed to advance a knife (not shown) between jaw members 110, 120 to cut tissue grasped therebetween. Activation switch 90, on the other hand, is selectively activatable to supply electrosurgical energy to one (or both) of jaw members 110, 120, as will be described in greater detail below.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "X-X" to rotate end effector 100 about longitudinal axis "X-X." Moveable handle 40 of handle assembly 30 is ultimately connected to a drive assembly (not shown) that, together, mechanically cooperate to impart movement of jaw members 110 and 120 between the spaced-apart position and the approximated position to grasp tissue disposed between jaw members 110, 120. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Referring to FIGS. 2-6, forceps 200 includes a one-piece handle assembly 207 (See FIG. 2), a shaft 12, and end effector 100. The one-piece handle 207 assembly includes a handle body 220 and a handle grip 205. An assembly pin 250 (See FIG. 3) and a grip pivot pin 215 (See FIG. 3) connect the handle grip 205 to the handle body 220. The grip pivot pin 215 is placed within a grip pivot pin bore 217 defined through the handle grip 205 and a grip pivot bore 218 defined through the handle body 220. Grip pivot pin 215 includes offset cam surfaces 219 that engage corresponding fulcrum bores (not shown) defined within the grip pivot pin bores 217 and 218. As the user moves the handle grip 205 perpendicular to a shaft axis E-E defined by the shaft 12 to control moveable jaw 110, the fulcrum bores defined within the grip pivot pin bores 217 and 218 serve to engage the cam surfaces 219 to prevent axial motion of the grip pivot pin 215 along axis B-B (See FIG. 5). The offset cam surfaces 219 assist in closing the jaw members 110 and 120, and therefore significantly reduce fatigue. Additionally, the width of the handle grip 205 may be substantially constrained to nest into a matching cavity 204 defined in the handle body 220 to constrain the handle grip 205 to planar fulcrum rotation perpendicular to the shaft axis E-E.

Figure 4:
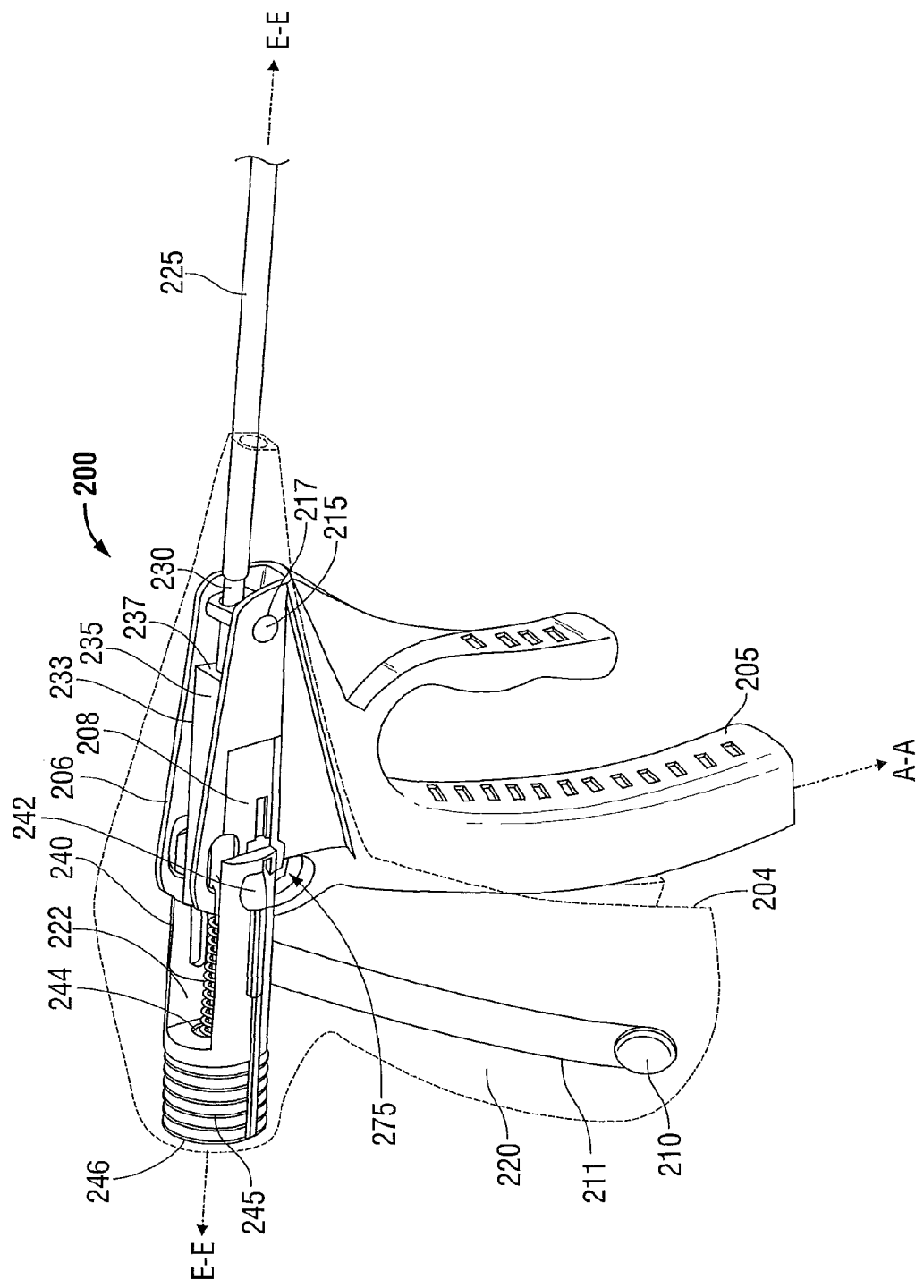
FIG. 4 is an internal perspective view of the one-piece handle assembly of the assembly shown in FIG. 3.

The grip pivot pin 215 further includes a cross bore 216 configured to receive the inner tube 230 therethrough (See FIG. 4). The diameter of the cross bore 216 is in close tolerance to the outside diameter of the inner tube 230, which prevents rotation of grip pivot pin 215 about axis B-B.

An assembly bore 273 is through-bored perpendicular to the shaft axis (axis E-E) through handle body 220. A longitudinal slot or assembly bore 275 is through-bored through the handle grip 205 perpendicular to the shaft axis (axis E-E) and extends along a portion of the handle grip 205. For example, the assembly bore 275 may be an arcuate slot extending along a portion of the handle grip 205 and configured to receive the assembly pin 250 therethrough. As the handle grip 205 is pivoted relative to the handle body 220 about the grip pivot pin 215, the assembly pin 250 translates along the assembly bore 275 (e.g., in a cam pin/cam slot type relationship). The assembly bore 275 closely matches the outer diameter of the assembly pin 250. The assembly bore 273 on the handle body 220 may be configured so that the assembly bore 275 on the handle grip 205 and the assembly bore 273 on the handle body 220 do not normally align. The assembly bore 275 may be configured with a relief slot 253 (See FIG. 6) to allow for installation of the assembly pin 250 through assembly bore 275 (on handle grip 205) and assembly bore 273 (on handle body 220) and then allow for longitudinal translation of the assembly pin 250 within assembly bore 275.

The assembly pin 250 includes offset cam surfaces 251 (See FIG. 6) that match cam surfaces 276 defined within assembly bore 275 on the handle grip 205. As the handle grip 205 is moved perpendicular to the shaft axis E-E and about grip pivot pin bore 217, the assembly pin 250 is translated along an axis D-D defined through the assembly bore 275 (See FIG. 6) a distance at least sufficient enough to open and close the jaws 110 and or 120 (See FIG. 1). Additionally, the mating cam slots and cam surfaces prevent axial movement motion of the assembly pin 250 along axis C-C.

Assembly pin 250 further includes a cross bore 279 bored perpendicular to axis C-C to allow a knife guide 265 to pass through. The tolerance of the cross bore 279 is closely matched to the outer diameter of the knife guide 265 to prevent rotation of the assembly pin 250 along axis C-C. Assembly pin 250 further includes a flat tab 252 (See FIG. 6) manufactured at each end of the assembly pin 250. The flat tabs 252 correspond to slots in the handle body 220 and the knife plunger 240 to further prevent rotation of the assembly pin 250 along axis C-C. Additionally, the flat tabs 252 prevent rotation of the knife plunger 240 and assembly pin 250 about axis E-E.

The handle body 220 includes a handle body bore 222 along the shaft axis (axis E-E) that closely matches the outer diameter of the knife plunger 240. The handle body bore 222 is counter-bored to a depth corresponding to the travel distance of a knife rod 270, where the counter-bore limits the travel of the knife plunger 240.

The knife plunger 240 is generally cylindrical in shape with two flanges 241 projecting proximally. The flanges 241 closely match the handle body bore 222 in the handle body 220 to align coaxially the knife plunger 240 along the shaft axis E-E. The flanges 241 are separated by a width in close tolerance to the outer width of the handle grip 205. The flanges 241 also include a cross-bored through hole or flange opening 282. The flange opening 282 is in close tolerance to the outside diameter of the assembly pin 250. The knife plunger 240 includes slots 242 on both sides that allow movement of the assembly pin 250 within the assembly bore 275. The slots 242 add in limiting rotation of the knife plunger 240 about shaft axis E-E.

The knife plunger 240 further includes one or more mechanisms or mechanical inter-engaging components that are engaged to attach a plunger cap 245 at a proximal end 246 of the knife plunger 240, which may include a screw, indent, etc. The plunger cap 245 may be snap fit, threaded, or attached in another suitable method to facilitate installation and/or removal from the knife plunger 240. The plunger cap 245 includes a coaxial counter bore (not shown) at the proximal end 246 to facilitate pushing of the knife rod 270 against the plunger cap 245. Axial forces applied along shaft axis E-E to the plunger cap 245 cause distal translation of the knife rod 270.

The knife plunger 240 further includes a knife plunger bore 244 disposed along the shaft axis E-E, where the diameter of the knife plunger bore 244 is in close tolerance to the outside diameter of a knife retainer 255. The knife retainer 255 is captured in a groove (not shown) defined in the knife rod 270 and pulls the knife rod 270 proximally by reacting with a knife spring 260. The knife spring 260 is held in compression between the proximal end face of the knife guide 265 and a distal side of knife retainer 255, which causes a constant separating force between the knife guide 265 and the plunger cap 245.

Additionally, a cam blocking function (not shown) may be included within the handle assembly 207 to prevent distal travel of the knife plunger 240 when the jaws 110, 120 are in the spaced-apart position. The geometry of the cam blocking function within handle grip 205 interferes with the flanges 241 of the knife plunger 240 to prevent movement of the flanges 241 when the jaws 110, 120 are in the spaced-apart position.

Figure 5:
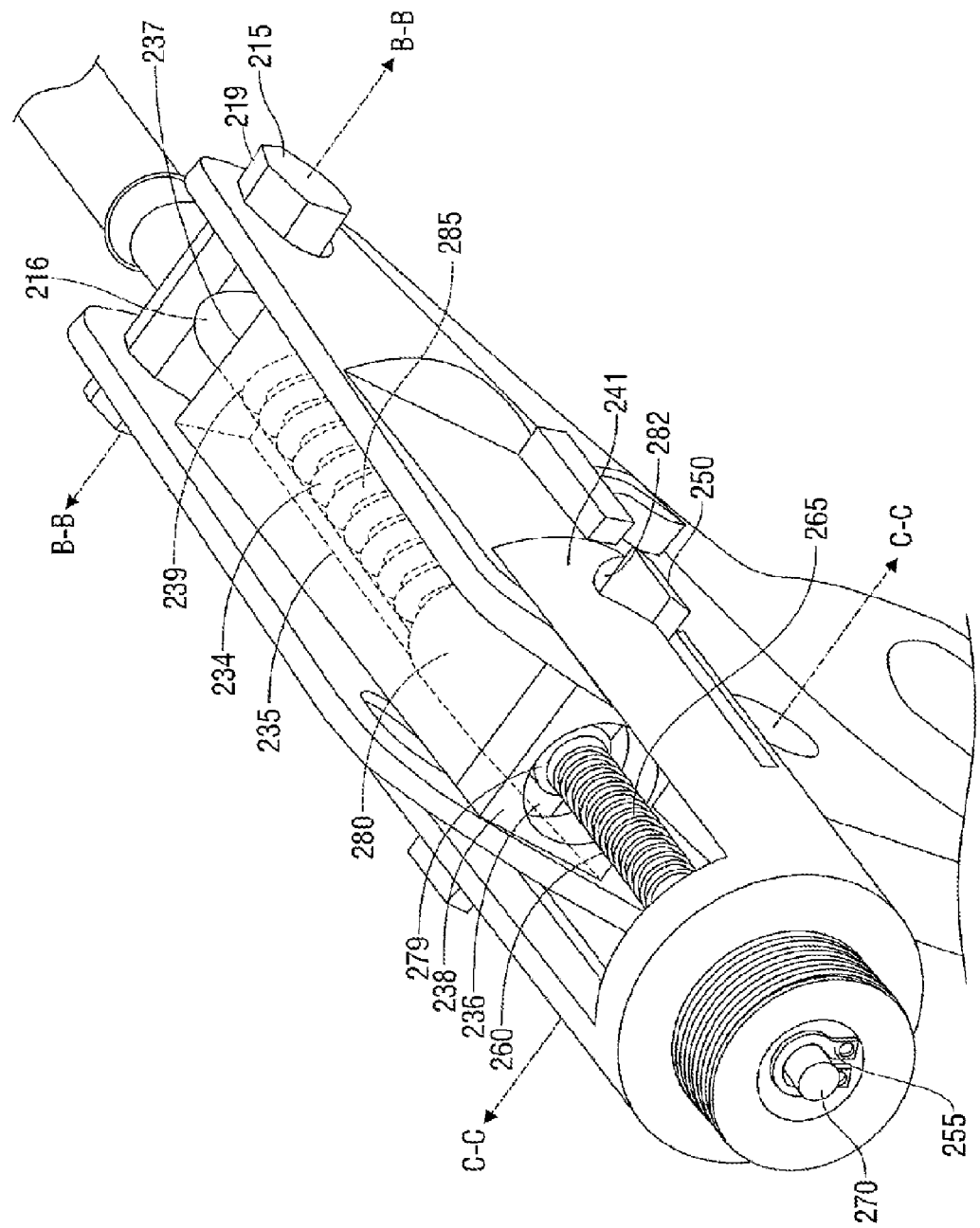
FIG. 5 is a top, perspective view of the one-piece handle assembly of the assembly shown in FIG. 3.
Figure 6:
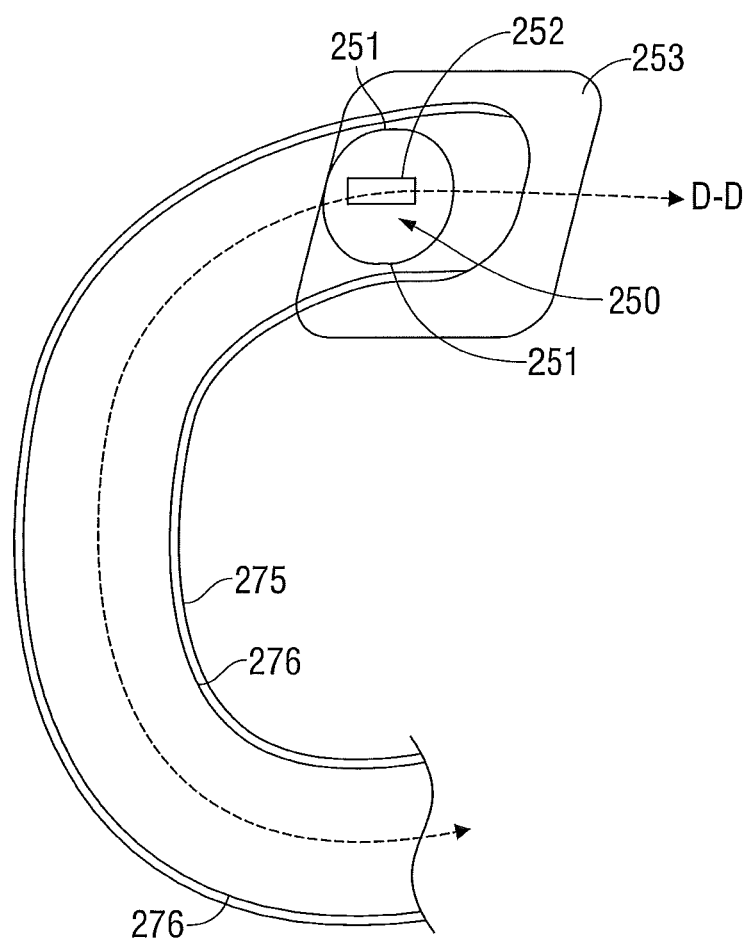
FIG. 6 is a detailed view of the assembly bore within the one-piece handle assembly.

As best shown in FIG. 5, installed within the handle grip 205 is a spring cartridge 235. The spring cartridge 235 includes a square bar 233 (see FIG. 4) of sufficient length to house a jaw spring 285. The width of the spring cartridge 235 closely matches a milled slot 206 defined within the handle grip 205 to prevent rotation or transverse translation of the spring cartridge 235 relative to the shaft axis (axis E-E). The spring cartridge 235 includes a hollow cavity 234, where the diameter of the hollow cavity 234 is in close tolerance to the outside diameter of the jaw spring 285 and the outer diameter of an inner tube bushing 280. At a distal end 237 of the spring cartridge 235, the spring cartridge 235 includes a cartridge bore 239 defined therein where the diameter of the cartridge bore 239 is in close tolerance to the outside diameter of an inner tube 230. The proximal end 238 of the spring cartridge 235 includes a cartridge cross bore 236 defined therein, where the diameter of the cartridge cross bore 236 is in close tolerance to the outside diameter of the assembly pin 250. The jaw spring 285 is compressed against an inner wall 239 the distal end 237 of the spring cartridge 235.

The shaft 12 includes an outer tube 225 and the inner tube 230. The inner tube includes a retaining ring and groove (not shown) at the proximal end of the inner tube 230 to provide a stop feature and facilitate assembly. The outer tube 225 is rigidly attached to the rigid jaw 120. The inner tube 230 is selectively translatable along shaft axis E-E and operatively connects to the moving jaw 110. To close moving jaw 110, a user rotates handle grip 205 about grip pivot pin 215, which results in proximal translation of assembly pin 250. The movement of assembly pin 250 is because of the handle grip 205 cam surface 276 relationship (See FIG. 6). The proximal translation of the assembly pin 250 causes proximal translation of the spring cartridge 235 because the spring cartridge 235 is coupled to the assembly pin 250. The proximal translation of the spring cartridge 235 causes compression of jaw spring 285. The compression of jaw spring 285 causes proximal translation of inner tube bushing 280, which results in proximal translation of inner tube 230 to which moving jaw 110 is attached.

Figure 7:
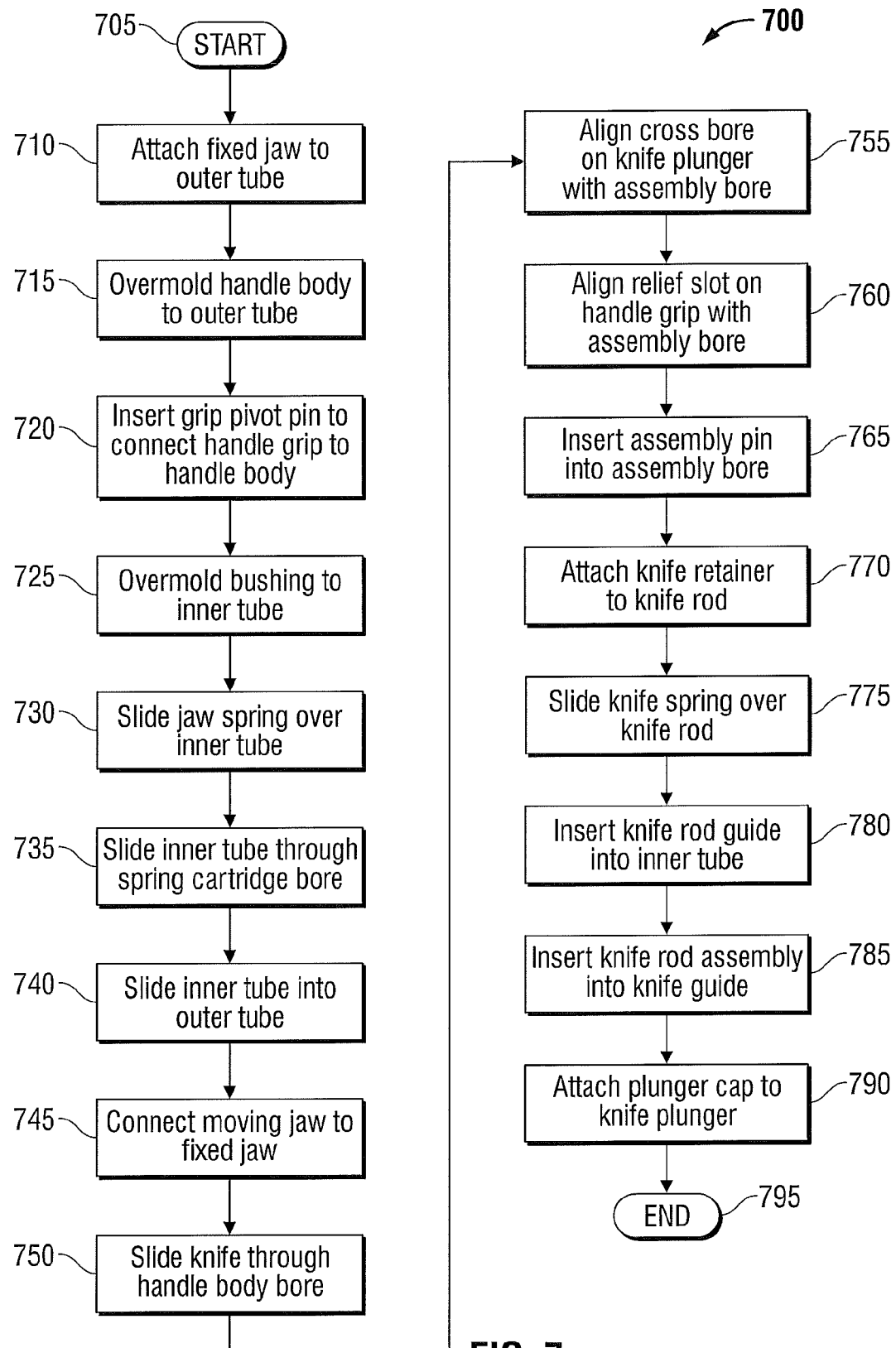
FIG. 7 is a flow chart for assembling a one-piece hand assembly according to the present disclosure.

FIG. 7 is a flow diagram of a process 700 for assembling a one-piece hand assembly 200. The process 700 starts at step 705 with an assembler attaching a fixed jaw 120 to an outer tube 225 at step 710. Next at step 715, the handle body 220 is overmolded onto the outer tube 225. Next the handle grip 205 is aligned with the handle body 220 in such a way that the grip pivot pin bore 218 in the handle body 220 and grip pivot pin bore 217 the handle grip 205 are aligned. The grip pivot pin bore 218 functions as a fulcrum when the handle grip 205 is moved perpendicular to axis A-A. Then at step 720, the grip pivot pin 215 is inserted within grip pivot pin bore 218 and grip pivot pin bore 217 to connect the handle grip 205 to the handle body 220.

Next at step 725, the inner tube bushing 280 is overmolded to the inner tube 230. The inner tube bushing 280 may also be overmolded after the handle body is overmolded to the outer tube 225. Then at step 730, the assembler slides the jaw spring 285 over the inner tube 230, where the proximal end of the jaw spring 285 contacts the inner tube bushing 280. Next the inner tube 230 is slid through the spring cartridge bore 239 at step 735. Then the inner tube 230 is slid into the outer tube 225 from the proximal end of the handle body 220 and through the cross bore 216 in the grip pivot pin 215 at step 740. Next at step 745, the moving jaw 110 is connected to the fixed jaw 120 with the pivot pin 103 while engaging jaw operating features knot shown) of the inner tube 230.

Then at step 750, the knife plunger 240 is slid through the handle body bore 222 in the handle body 220. Next at step 755, the cross bore 242 is aligned within the flanges 241 on the knife plunger 240 with the assembly bore 273 on the handle body 220. At step 760, the relief slot 253 is aligned on the handle grip 205 with assembly bore 273 on the handle body 220. While compressing the inner tube bushing 280 distally, the assembler inserts the assembly pin 215 into the assembly bore 273, 275 at step 765, which engages the cross bore 242 in the knife plunger 240 and the spring cartridge 235. Inserting the assembly pin 215 also aligns the flanges 241 with the flat tabs 208 on the handle grip 205. The assembler then releases the compression applied to the inner tube bushing 280. Next at step 770, the assembler attaches the knife retainer 255 to the knife rod 270. At step 775, the knife spring 260 is slid over the knife rod 270. Next, the knife guide 265 is inserted into inner tube 230 at step 780. The knife rod assembly, including the knife spring 260, knife retainer 255 and knife rod 270, is slid into the proximal end of the knife guide 265 at step 785. The process 700 ends at step 795 after the assembler attaches plunger cap 245 to the knife plunger at step 790. The process 700 does not include any welds, adhesives, or fasteners in completing the final assembly of the one-piece handle assembly 200.

Additionally, the assembler routes any electrical wires 211 to an electrical connector 210 (See FIG. 4) through the one piece handle assembly 200 during assembly or after completing assembly. In some embodiments, the electrical wires 211 are placed within the assembly 200 as outer tube 225, inner tube 230, knife guide 265, or knife rod 270 are installed and termination of the electrical wires 211 is done last. Electrical wires 211 from jaw members 110 and 120 may be routed between outer tube 225 and inner tube 230, between the inner tube 230 and knife guide 265, between the knife guide 265 and the knife rod 270, and/or through the knife rod 270. All entry and exit points for the electrical wires 211 may be suitably slotted into these components. Alternatively, through the use of conductive and/or insulative materials, these components may themselves be used for electrical/RF current transfer in combination with termination wiring. One or more passageways (not shown) may be molded into handle body 220 to allow for termination of the electrical wires 211 to snap in electrical connector 210.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A method for assembling a surgical instrument, comprising:
attaching a fixed jaw to an outer tube, the outer tube defining a longitudinal axis;
overmolding a handle body to the outer tube;
aligning a pivot pin bore disposed through the handle body with a pivot pin bore disposed through a handle grip;
inserting a pivot pin through the pivot pin bore disposed through the handle body and the pivot pin bore disposed through the handle grip to connect the handle grip to the handle body at a first location along the longitudinal axis;
inserting an inner tube into the outer tube;
connecting a moving jaw to the fixed jaw after attaching the fixed jaw to the outer tube;

connecting the moving jaw to the inner tube after inserting the inner tube into the outer tube; and inserting an assembly pin through an assembly bore disposed through the handle body and a longitudinal assembly bore disposed through the handle grip to connect the handle grip to the handle body at a second location spaced along the longitudinal axis from the first location, the handle grip configured to pivot relative to the handle body about the pivot pin to translate the assembly pin along the longitudinal assembly bore and pivot the moving jaw relative to the fixed jaw.

2. The method according to claim 1, wherein the fixed jaw is connected to the moving jaw by an end effector pivot pin.

3. The method according to claim 1, further comprising:
overmolding a bushing to the inner tube;
sliding a jaw spring over the inner tube prior to inserting the inner tube into the outer tube, wherein a proximal end of the jaw spring contacts the bushing; and
sliding the inner tube through a spring cartridge bore in a spring cartridge prior to inserting the inner tube into the outer tube.

4. The method according to claim 3, further comprising:
compressing the bushing distally prior to inserting the assembly pin; and
releasing the compression after inserting the assembly pin.

5. The method according to claim 3, wherein inserting the assembly pin includes aligning the spring cartridge with the assembly bore disposed through the handle body and the longitudinal assembly bore disposed through the handle grip.

6. The method according to claim 1, further comprising:
sliding a knife plunger through a handle body bore in the handle body;
aligning a cross bore on the knife plunger with the assembly bore disposed through the handle body prior to inserting the assembly pin;
aligning a relief slot on the handle grip with the assembly bore disposed through the handle body prior to inserting the assembly pin;
engaging the knife plunger with the assembly pin;
attaching a knife retainer to a knife rod;
sliding a knife spring over the knife rod and against a knife retainer to create a knife rod assembly;
inserting a knife guide into the inner tube; and
inserting the knife rod assembly into a proximal end of the knife guide.

7. The method according to claim 6, further comprises attaching a plunger cap to the knife plunger.

8. The method according to claim 7, wherein inserting the assembly pin further comprises aligning a pair of flanges disposed on the plunger cap with a pair of corresponding flat surfaces disposed on the handle body.

9. The method according to claim 8, wherein the pair of flanges limit rotation of the knife plunger about an axis defined through the knife plunger.

10. The method according to claim 6, further comprising preventing the knife plunger from travelling distally when the fixed jaw and the moving jaw are in a spaced-apart position.

11. The method according to claim 1, further comprising:
routing electrical wires connected to the fixed jaw and the moving jaw through the outer tube; and
electrically connecting the electrical wires to a generator via an electrosurgical cable.

12. A method for assembling a surgical instrument, comprising:

aligning a pivot pin bore disposed through a handle body with a pivot pin bore disposed through a handle grip;
inserting a pivot pin through the pivot pin bore disposed through the handle body and the pivot pin bore disposed through the handle grip to connect the handle grip to the handle body at a first location;
inserting an inner tube into an outer tube;
connecting a moving jaw to a fixed jaw attached to the outer tube;
connecting the moving jaw to the inner tube after inserting the inner tube into the outer tube; and
inserting an assembly pin through an assembly bore disposed through the handle body and a longitudinal assembly bore disposed through the handle grip to connect the handle grip to the handle body at a second location longitudinally spaced from the first location, the handle grip configured to pivot relative to the handle body about the pivot pin to translate the assembly pin along the longitudinal assembly bore and pivot the moving jaw relative to the fixed jaw.

13. The method according to claim 12, wherein the assembly bores are disposed proximal to the pivot pin bores along a longitudinal axis defined by the outer tube.

14. The method according to claim 12, wherein inserting the inner tube into the outer tube includes inserting the inner tube through the pivot pin after inserting the pivot pin through the pivot pin bores.

15. The method according to claim 12, wherein the second location is longitudinally spaced from the first location along a longitudinal axis defined by the outer tube.

16. A method for assembling a surgical instrument, comprising:
attaching a fixed jaw to an outer tube;
overmolding a handle body to the outer tube;
aligning a pivot pin bore disposed through the handle body with a pivot pin bore disposed through a handle grip;
inserting a pivot pin through the pivot pin bore disposed through the handle body and the pivot pin bore disposed through the handle grip to connect the handle grip to the handle body at a first location;
inserting an inner tube into the outer tube;
connecting a moving jaw to the fixed jaw after attaching the fixed jaw to the outer tube;
connecting the moving jaw to the inner tube after inserting the inner tube into the outer tube;
aligning a cross bore on a knife plunger with an assembly bore disposed through the handle body;
aligning a relief slot on the handle grip with the assembly bore disposed through the handle body;
inserting an assembly pin through the assembly bore disposed through the handle body and an assembly bore disposed through the handle grip to connect the handle grip to the handle body at a second location and to engage the knife plunger with the assembly pin, the handle grip configured to move relative to the handle body to pivot the moving jaw relative to the fixed jaw;
sliding the knife plunger through a handle body bore in the handle body;
attaching a knife retainer to a knife rod;
sliding a knife spring over the knife rod and against a knife retainer to create a knife rod assembly;
inserting a knife guide into the inner tube; and
inserting the knife rod assembly into a proximal end of the knife guide.

* * * * *